(12) United States Patent
Ishii et al.

(10) Patent No.: US 8,877,027 B2
(45) Date of Patent: Nov. 4, 2014

(54) LIQUID ANALYZER

(71) Applicant: Horiba, Ltd., Kyoto (JP)

(72) Inventors: Akio Ishii, Kyoto (JP); Issei Kobayashi, Kyoto (JP)

(73) Assignee: Horiba, Ltd. (JP)

( * ) Notice: Subject to any disclaimer, the term of this patent is extended or adjusted under 35 U.S.C. 154(b) by 0 days.

(21) Appl. No.: 13/947,518

(22) Filed: Jul. 22, 2013

(65) Prior Publication Data

US 2014/0048426 A1 Feb. 20, 2014

(30) Foreign Application Priority Data

Jul. 23, 2012 (JP) .................................. 2012-163164

(51) Int. Cl.
*G01N 27/333* (2006.01)
*G01N 27/404* (2006.01)
*G01N 27/30* (2006.01)

(52) U.S. Cl.
CPC ............ *G01N 27/301* (2013.01); *G01N 27/404* (2013.01); *G01N 27/30* (2013.01)
USPC .......................................... 204/416; 204/418

(58) Field of Classification Search
CPC ................. G01N 27/333–27/401; G01N 27/36
See application file for complete search history.

(56) References Cited

U.S. PATENT DOCUMENTS 5,840,168 A * 11/1998 Chaniotakis et al. ......... 204/416

FOREIGN PATENT DOCUMENTS

| DE | 2337081 A1 * | 7/1974 | ............ G01N 27/52 |
|----|--------------|--------|--------------------------|
| JP | 62-148648 A | 7/1987 | |
| JP | 01-209352 A | 8/1989 | |
| JP | 01-295158 A | 11/1989 | |
| JP | 2000-146899 A | 5/2000 | |

OTHER PUBLICATIONS

Derwent English language abstract of Dolezal et al. DE 2337081 A1, patent published Jul. 11, 1974.*
CAPLUS STN Englsih language abstract of Dolezal et al. DE 2337081 A1, patent published Jul. 11, 1974.*
EPO computer-generated English language translation of the Description section of Dolezal et al. DE 2337081 A1, patent published Jul. 11, 1974.*

(Continued)

*Primary Examiner* — Alex Noguerola
(74) *Attorney, Agent, or Firm* — Cantor Colburn LLP (57) ABSTRACT

A liquid analyzer may include a reference electrode provided with internal liquid containing a halide ion; and an ion electrode of which a measurable concentration range for a measuring target ion is lower than the concentration of the halide ion in the internal liquid of the reference electrode, The internal liquid of the ion electrode contains the measuring target ion and a halide ion; and the internal liquid of the ion electrode is liquid in which the concentration of the measuring target ion and the halide ion are regulated such that an osmotic pressure and an isothermal point of the internal liquid of the ion electrode respectively have desired values, and the isothermal point is included in the measurable concentration range, and the concentration of the halide ion is different from the concentration of the halide ion in the internal liquid S33 of the reference electrode.

4 Claims, 7 Drawing Sheets

CROSS-SECTIONAL VIEW
ALONG B-B/C-C LINE

(56) References Cited

OTHER PUBLICATIONS

Chinese Patent Office computer-generated English language translation of the claim in and Description of CN 101403761 A, patent published Apr. 8, 2009.*

Chinese Patent Office computer-generated English language translation of the Abstract of CN 101403761 A, patent published Apr. 8, 2009.*

S. Capelo, et al., In situ continuous monitoring of chloride, nitrate and ammonium in a temporary stream, Comparison with standard methods, Talanta, Bd. 71, 2007, pp. 1166-1171.

German Office Action issued by the German Patent and Trade Mark Office on Jun. 4, 2014, for Application No. 10 2013 214 384.2, with full translation.

Metrohm AG, Switzerland, NH3-selective electrodes, Manual, 8.109.8031EN, Nov. 2011 ebe, pp. 1-19.

M.B. Saleh, "Neutral carrier-based magnesium-selective electrode", Journal of Electroanalytical Chemistry, Bd. 373, 1994, pp. 89-95.

* cited by examiner

CROSS-SECTIONAL VIEW
ALONG B-B/C-C LINE

LIQUID ANALYZER

The present invention claims priority under 35 U.S.C. §119 to Japanese Application No. 2012-163164 filed Jul. 23, 2012, the entire content of which is incorporated herein by reference.

TECHNICAL FIELD

This invention relates to a liquid analyzer provided with an ion electrode that is preferable for the case of setting a sample having low ion concentration, such as environmental water, as a measuring target.

BACKGROUND ART

As an electrode for electrochemically measuring the concentration of an ion such as an ammonium ion with setting environmental water such as river water, lake water, or seawater, water or wastewater, industrial wastewater, or the like as a sample, a liquid membrane type ion electrode is known (Patent Literature 1).

Figure 7:
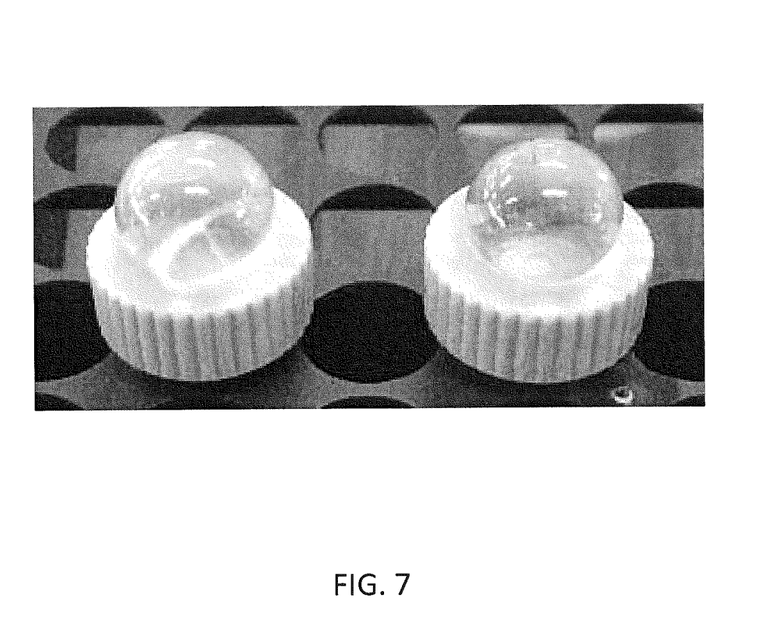
FIG. 7 is a photograph illustrating a responsive membrane of a conventional ammonium ion electrode.

As a responsive membrane of this sort of ion electrode, a membrane having properties of a semipermeable membrane is used; however, in the case where ion concentration of the total of solutes of internal liquid is far higher than ion concentration of a sample, due to a difference in osmotic pressure between the sample and the internal liquid, water molecules on the sample side permeate the internal liquid side, and therefore an indicated value may vary, or in some cases, as illustrated in FIG. 7, the responsive membrane may expand and finally explode. For example, in the case where a difference between the ion concentration of the salt components of the internal liquid of the ion electrode (internal liquid used for an ion electrode or a reference electrode is considered to almost consist of salt components) and the ion concentration of the total of solutes of the sample is 6.55 M, a calculational difference in osmotic pressure is as much as 16.4 MPa.

On the other hand, in the case of decreasing the ion concentration of the salt components of the internal liquid, there is a problem that making the concentration of a halide ion contained in the internal liquid of the ion electrode coincide with the concentration of a halide ion contained in internal liquid of a reference electrode (a salt component used for such internal liquids is generally a halide metal salt, for example, KCl), which is generally performed, is impossible, and therefore a so-called isothermal point at which a membrane potential does not change even as temperature is changed shifts from a measurable range to increase a measurement error associated with a temperature change.

CITATION LIST

Patent Literature

Patent Literature 1: JP-A-2000-146899

SUMMARY OF INVENTION

Technical Problem

Therefore, the present invention is made in order to provide a liquid analyzer provided with an ion electrode that, even in the case where a responsive membrane is one having properties of a semipermeable membrane and a sample of which total ion concentration of solutes is low is set as a measuring target, prevents water molecules from permeating internal liquid and further keeps a measurement error associated with a temperature change small.

Solution to Problem

That is, a liquid analyzer according to the present invention is provided with: a reference electrode that is provided with internal liquid containing a halide ion and an internal electrode in contact with the internal liquid in a space communicatively connected outside through a liquid junction part; and an ion electrode that is provided with internal liquid and an internal electrode in contact with the internal liquid in a space separated from outside by a responsive membrane, and has a measurable concentration range for a measuring target ion, the measurable concentration range being lower than concentration of the halide ion in the internal liquid of the reference electrode, wherein: the internal liquid of the ion electrode contains the measuring target ion and a halide ion; and the internal liquid of the ion electrode is liquid in which concentration of the measuring target ion and concentration of the halide ion in the internal liquid of the ion electrode are regulated such that an osmotic pressure and an isothermal point of the internal liquid of the ion electrode respectively have desired values, and the isothermal point is included in the measurable concentration range, and the concentration of the halide ion is different from the concentration of the halide ion in the internal liquid of the reference electrode.

The following expression (1) is an expression for calculating a membrane potential of the responsive membrane of the ion electrode such as an ammonium ion electrode connected to the reference electrode. Note that configurations of the ammonium ion electrode and the reference electrode used together are as follows:

<Ammonium Ion Electrode>
Internal electrode: Ag/AgCl electrode
Internal liquid: $NH_4Cl$ solution
<Reference Electrode>
Internal electrode: Ag/AgCl electrode
Internal liquid: KCl saturated liquid

[Expression 1]

$$E = E^\circ_{Ion} + \frac{RT}{F} \ln \left( \overbrace{\underbrace{a_{N,Sample}}_{C}}^{B} \times \overbrace{\underbrace{a_{Cl,Ref}}_{a_{Cl,Ion}}}^{A} \right) \quad (1)$$

Here, respective parameters in the expression (1) are as follows:
E: a membrane potential (mV) of the responsive membrane of the ammonium ion electrode,
$E^O_{Ion}$: a standard electrode potential (mV) for the ammonium ion electrode,
R: the gas constant,
F: the Faraday constant,
T: absolute temperature (K),
$a_{N,Sample}$: $NH_4^+$ ion activity (mol/L) in the sample,
$a_{N,Ion}$: $NH_4^+$ ion activity (mol/L) in the internal liquid of the ammonium ion electrode, $a_{Cl,Ref}$: Cl⁻ ion activity (mol/L) in the internal liquid of the reference electrode, and $a_{Cl,Ion}$: Cl⁻ ion activity (mol/L) in the internal liquid of the ammonium ion electrode.

In the past, it has been considered that in order to minimize a temperature-caused measurement error of an Ag/AgCl electrode, Cl⁻ ion activity (ion concentration) in internal liquid of a reference electrode and Cl⁻ ion activity (ion concentration) in internal liquid of an ion electrode should be made equal to each other. For this reason, the internal liquid has been prepared such that A and C terms surrounded by dashed lines in the expression (1) become equal to 1. In order to stabilize a potential, a large amount of KCl or the like has been added, so that chloride (halide) ion activity of the reference electrode has been large, and therefore in the case of measuring a sample having low solute ion concentration, water molecules have permeated the ion electrode. However, the present inventors have arrived at the fact that by regulating the ion activities (ion concentrations) of the respective ions such that the whole of a B term surrounded by a solid line in the expression (1) becomes equal to 1, an isothermal point can be obtained even in the case where the chloride (halide) ion activities in the internal liquids of the reference and ion electrodes are different from each other. As a result, the present inventors have successfully obtained the isothermal point within a desired concentration range even though reducing the concentration of an electrolyte in the internal liquid of the ion electrode.

For this reason, according to the present invention, by varying the concentration of the measuring target ion and the concentration of the halide ion in the internal liquid, while the preparation is made such that the osmotic pressure of the internal liquid reaches the same level as the osmotic pressure of the sample, the isothermal point can be obtained within the measurement range of the measuring target ion, so that even in the case where the responsive membrane is a membrane having properties of a semipermeable membrane and the sample having low ion concentration is set as a measuring target, water molecules do not permeate the internal liquid, and further, a measurement error associated with a temperature change can be reduced.

As the internal electrode of the ion electrode, for example, an Ag/AgCl electrode is used.

As the measuring target ion of the ion electrode, without particular limitation, an ammonium ion or the like that serves as an index in the case of, as a sample, setting environmental water such as river water, lake water, or seawater, water or wastewater, industrial wastewater, or the like to evaluate a contamination level of the sample is cited.

A method for preparing the internal liquid of the ion electrode is also one aspect of the present invention. That is, the method for preparing the internal liquid of the ion electrode according to the present invention is a method for preparing internal liquid of an ion electrode that is provided with the internal liquid and an internal electrode in contact with the internal liquid in a space separated from outside by a responsive membrane, and has a measurable concentration range for a measuring target ion, the measurable concentration range being lower than concentration of a halide ion in internal liquid of a reference electrode, wherein: the internal liquid of the ion electrode contains the measuring target ion and a halide ion; and the internal liquid of the ion electrode is prepared on a basis of concentration of the measuring target ion and concentration of the halide ion in the internal liquid of the ion electrode, the internal liquid being prescribed such that the concentration of the halide ion in the internal liquid of the ion electrode is different from the concentration of the halide ion in the internal liquid of the reference electrode, such that an osmotic pressure and an isothermal point of the internal liquid of the ion electrode respectively have desired values, and the isothermal point is included in the measurable concentration range.

Advantageous Effects of Invention

As described above, according to the present invention, a liquid analyzer provided with an ion electrode that, even in the case where a responsive membrane has properties of a semipermeable membrane, and a sample having low ion concentration is set as a measuring target, prevents water molecules from permeating internal liquid, and further keeps a measurement error associated with a temperature change small can be obtained.

DESCRIPTION OF EMBODIMENTS

In the following, one embodiment of the present invention is described with reference to the drawings.

A liquid analyzer of the present embodiment is an ammonia meter 100 that, as analyzing target liquid L, for example, sets wastewater being treated in an aeration tank where ammonia nitrogen is treated by microorganisms in a wastewater treatment process, and is used for monitoring the concentration of an ammonium ion contained in the wastewater. The wastewater in the aeration tank is generally wastewater having low solute concentration.

More specifically, the ammonia meter 100 is one integrated with three sensors S1, S2, and S3, and as the sensors S1, S2, and S3, provided with: a reference electrode (reference electrode) S3 for measuring a reference potential; an ammonium ion electrode S1 for measuring a potential due to an ammonium ion; and a potassium ion electrode S2 for measuring a potential due to a potassium ion, which is used to correct interference with the ammonium ion caused by the potassium ion.

Figure 1:
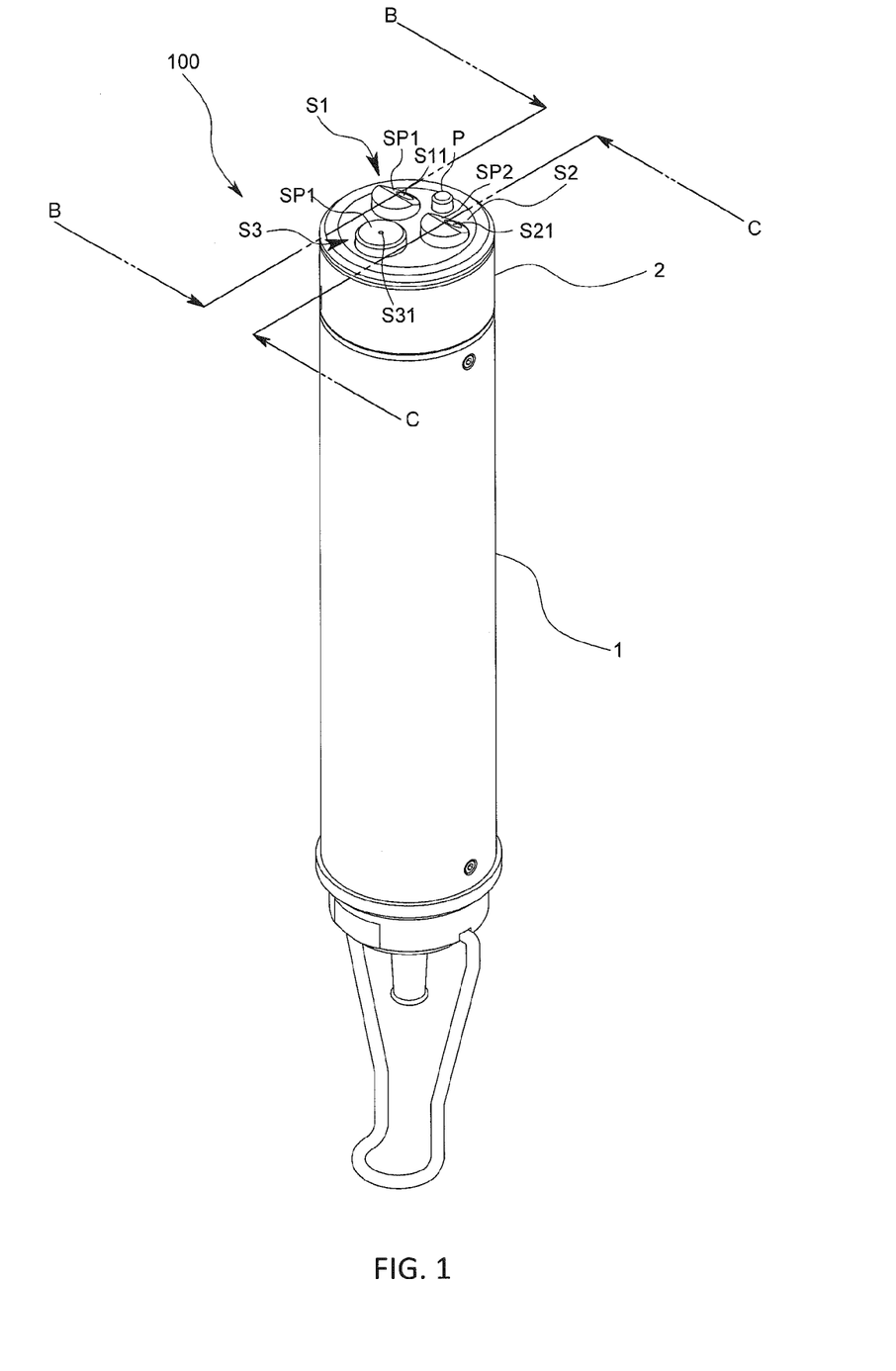
FIG. 1 is a schematic overall perspective view of an ammonia meter according to one embodiment of the present invention.

As illustrated in a perspective view of FIG. 1, the ammonia meter 100 has a substantially thin cylindrical housing, and configured such that on a base end side thereof, a carrying chain is provided, and on a fore end surface, sensor planes SP1, SP2, and SP3 of the three sensors S1, S2, and S3 are exposed outside. Note that the sensor planes SP1, SP2, and SP3 refer to planes formed with responsive membranes S11 and S21, and a liquid junction part S31 of the respective electrodes.

Figure 2:
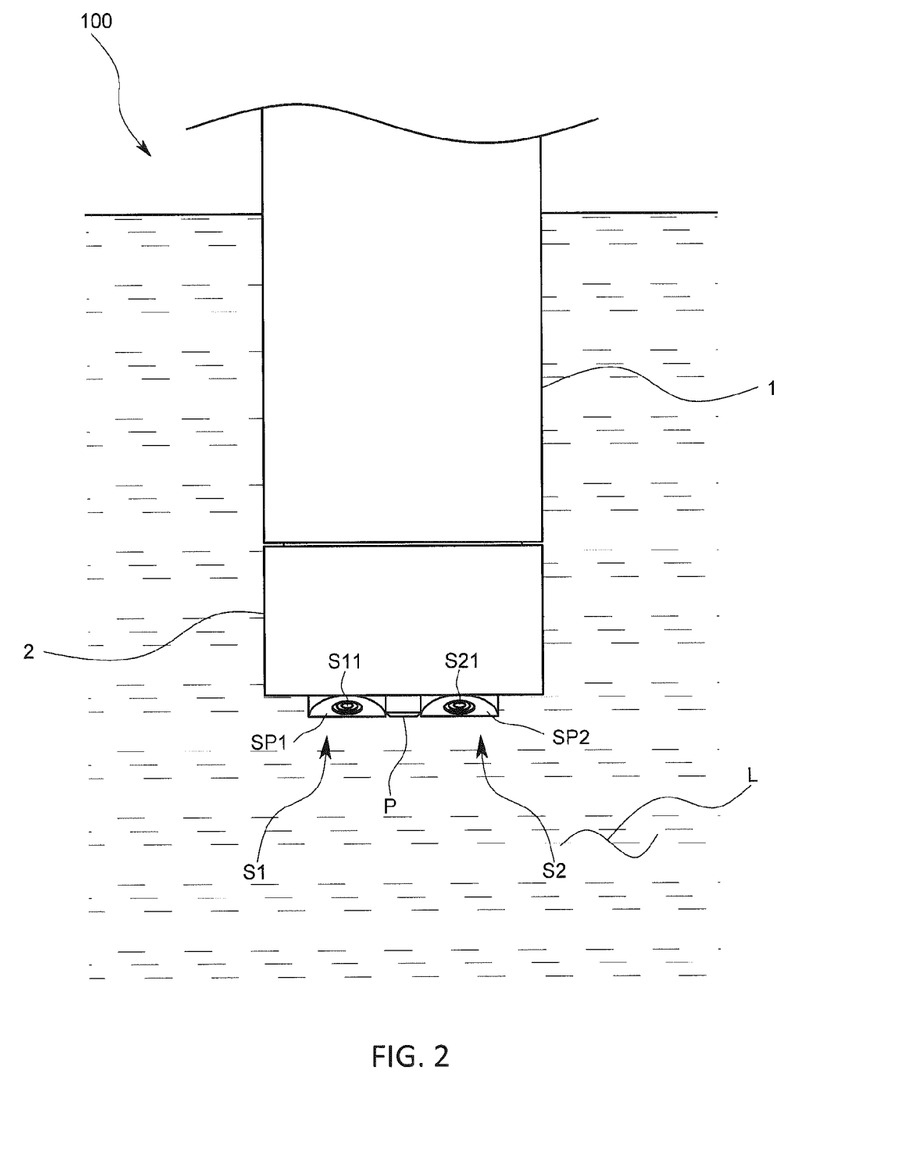
FIG. 2 is a schematic diagram illustrating a specification aspect of the ammonia meter in the same embodiment.

Also, as illustrated in a schematic diagram of FIG. 2, the ammonia meter 100 is one that is immersed such that the fore end surface of the ammonia meter 100 face vertically downward in the analyzing target liquid L, and with the sensor planes SP1, SP2, and SP3 of the respective sensors S1, S2, and S3 being immersed in the analyzing target liquid L, measures the respective potentials to measure the ammonium ion concentration in the analyzing target liquid L. As can be seen from FIGS. 1 and 2 as well, in order to prevent air bubbles from accumulating on the sensor planes SP1 and SP2 during the analysis, the two of the three sensors S1, S2, and S3 are provided with the sensor planes SP1 and SP2 being tilted with respect to an axial direction of the housing. Further, the two tilted sensor planes SP1 and SP2 are configured such that the surfaces thereof face the same predetermined direction.

The respective parts are further described.

Figure 3:
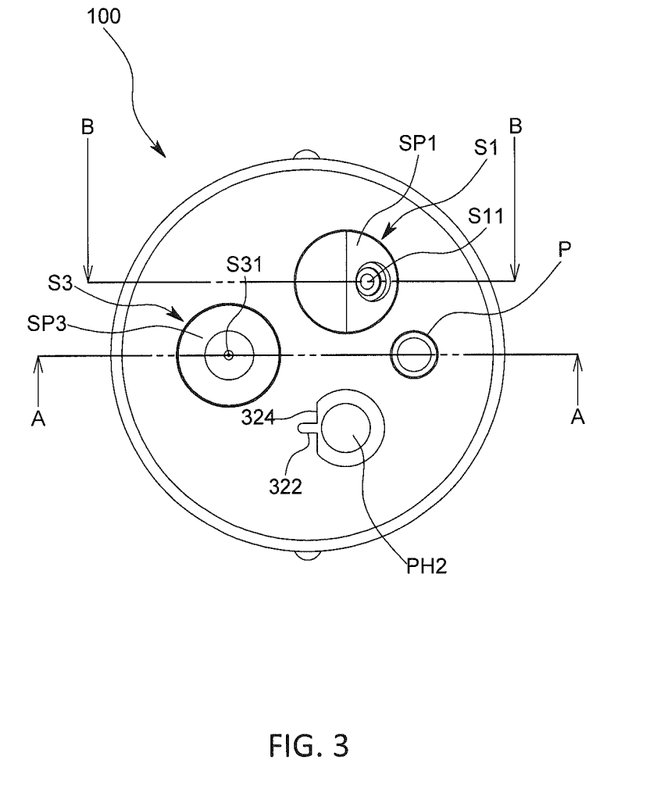
FIG. 3 is a schematic diagram illustrating a fore end surface of the ammonia meter in the same embodiment in a state where a pressing mechanism is removed.

FIG. 3 illustrates a plan view of the fore end surface of the ammonia meter 100. The fore end surface of the ammonia meter 100 is formed in a circular shape, and on one center line of the fore end surface, which laterally extends in the view, the sensor plane SP3 of the reference electrode S3 and an aftermentioned thermometer protecting tube P are arranged side by side. Also, in positions slightly displaced from another center line that vertically extends in the view, a fore end part of the ammonium ion electrode S1 and a fore end of the potassium ion electrode S2 are arranged side by side in line. In the following description, the description is provided also with reference to FIG. 4 that is a cross-sectional view prepared by cutting along an A-A line illustrated in FIG. 3, and FIG. 5 that is a cross-sectional view prepared by cutting along a B-B or C-C line. Note that cross-sections prepared by the cutting along the B-B and C-C lines appear to be substantially symmetric, and are therefore illustrated with being typified by one view of FIG. 5.

Figure 4:
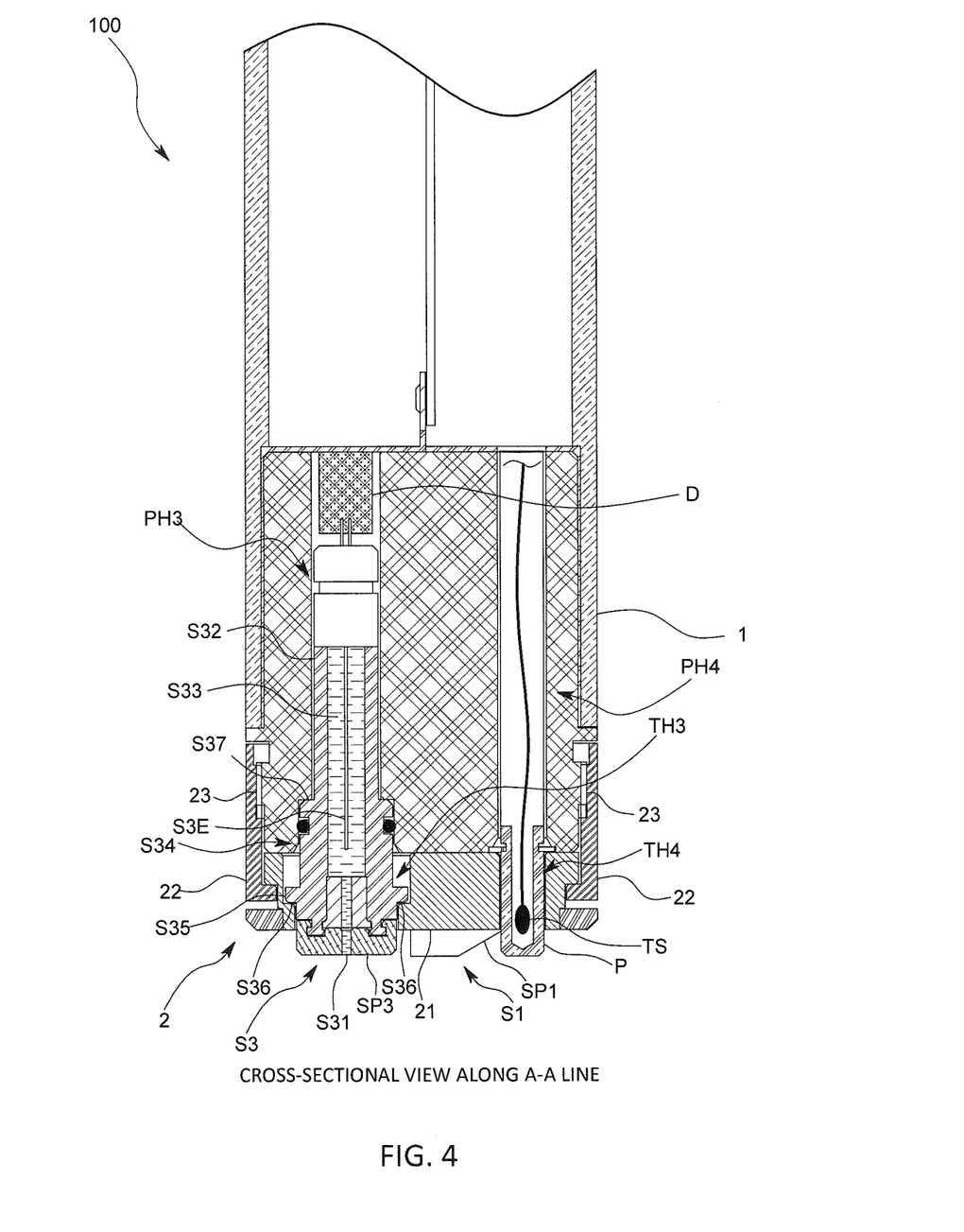
FIG. 4 is a schematic partial enlarged view of an A-A line cross-section of the ammonia meter in the same embodiment.
Figure 5:
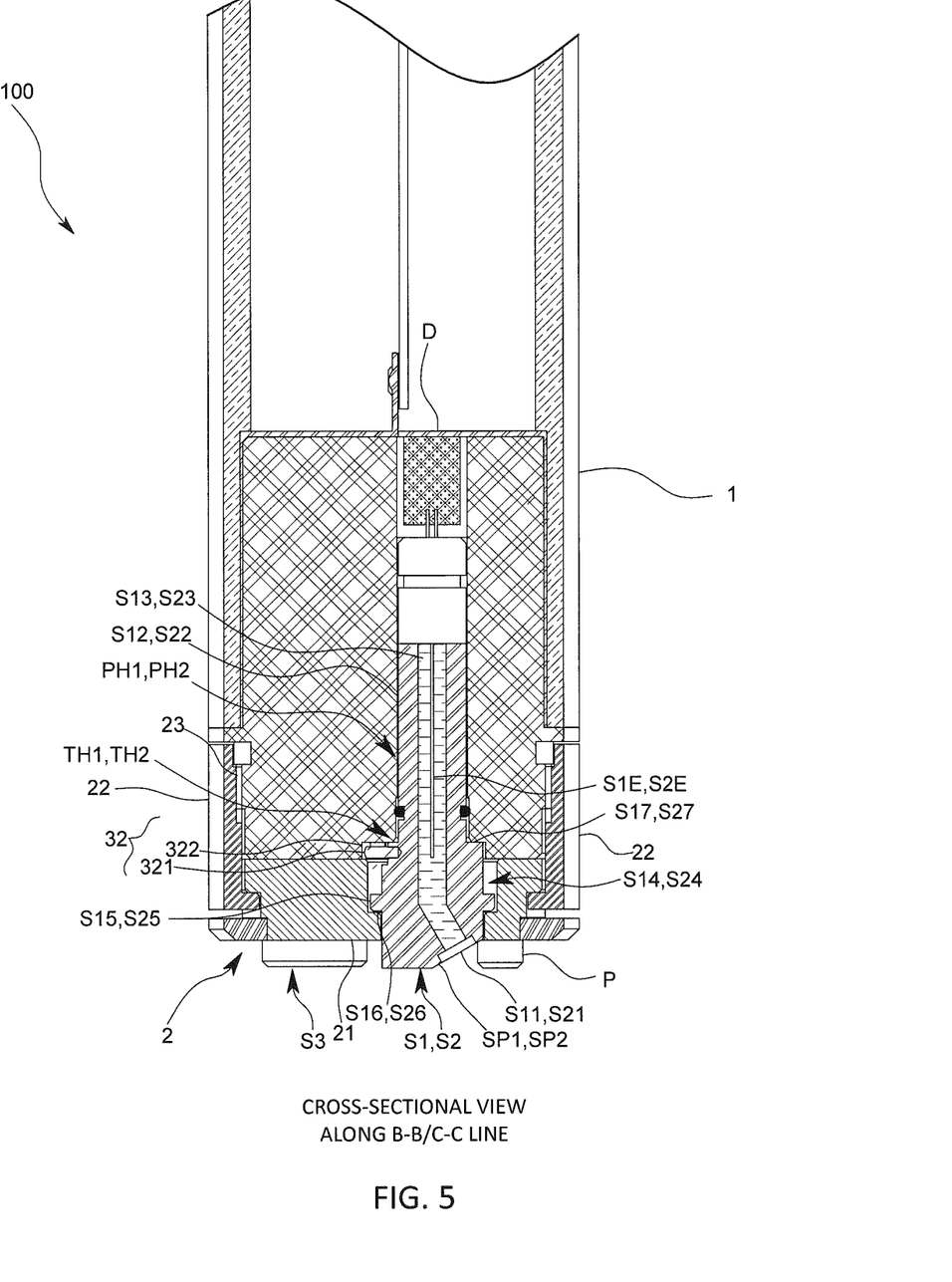
FIG. 5 is a schematic partial enlarged view of a B-B or C-C line cross-section of the ammonia meter in the same embodiment.

As illustrated in the respective cross-sectional views, the ammonia meter 100 is configured to include: a body 1 that is formed in a substantially cylindrical shape that has a hollow part on a base end side and is formed with a solid part on a fore end side; the three sensors S1, S2, and S3 that are inserted into the body 1; and a pressing mechanism 2 that is provided so as to cover the fore end side of the body 1 and presses the three cap-like sensors S1, S2, and S3 against the body 1 to fix them.

In the body 1, four insertion holes PH1, PH2, PH3, and PH4 extending in the axial direction are formed, into which the three sensors S1, S2, and S3 and the thermometer protecting tube P that are respectively formed in substantially cylindrical shapes are inserted. Also, the insertion holes PH1, PH2, and PH3 are not formed with any female screw, but simply inserted with the respective sensors S1, S2, and S3. In addition, the thermometer protecting tube P is fixed to the insertion hole PH4 to prevent from being removed. Also, inside the thermometer protecting tube P, a temperature sensor TS that measures a temperature used to perform temperature compensation for measured values of the respective sensors S1, S2, and S3 is contained.

To describe parts common to the three sensors S1, S2, and S3, as can be seen from the respective drawings, the respective sensors S1, S2, and S3 have support tubes S12, S22, and S32 that are formed in substantially cylindrical shapes and made of resin, and inside the support tubes S12, S22, and S32, internal liquids S13, S23, and S33, and internal electrodes S1E, S2E, and S3E immersed in the internal liquids S13, S23, and S33 are contained. Fore ends of the support tubes S12, S22, and S32 are formed with opening parts, and provided with the responsive membranes S11 and S21, and the liquid junction part S31 so as to block the opening parts, respectively. Also, on outer circumferential surfaces of the support tubes S12, S22, and S32, O-rings are provided, which are configured to form axial seals between the support tubes S12, S22, and S32 and the insertion holes PH1, PH2, and PH3, respectively. Further, the present embodiment is adapted such that base ends of the respective sensors S1, S2, and S3 are in contact with electrode terminals Ds at innermosts of the insertion holes PH1, PH2, and PH3, and the respective potentials obtained are transferred from the electrode terminals Ds to an external arithmetic unit. Also, to further describe parts common to external shapes of the support tubes S12, S22, and S32 in detail, the support tubes S12, S22, and S32 of the respective sensors S1, S2, and S3 have thick cylindrical parts S14, S24, and S34 of which diameters of fore end parts are larger than those on base end part sides, and base end side end surfaces of the thick cylindrical parts S14, S24, and S34 engage with step parts formed on the insertion holes PH1, PH2, and PH3 to fulfill functions as body contact surfaces S17, S27, and S37 that come into contact with the body 1. Also, in central parts of outer circumferential surfaces of the thick cylindrical parts S14, S24, and S34, ring-shaped protrusion parts S15, S25, and S35 protruding in radial directions are formed, and fore end side flat surfaces of the protrusion parts S15, S25, and S35 is formed as engaging parts S16, S26, and S36 that engage with the pressing mechanism 2, respectively. That is, the engaging parts S16, S26, and S36 are pressed by the pressing mechanism 2 toward the body 1 side, whereby the body contact surfaces S17, S27, and S37 are pressed against the body 1, and consequently the respective sensors S1, S2, and S3 are fixed to the body 1 by a predetermined force.

Among the three sensors S1, S2, and S3, the reference electrode S3 of which the sensor plane SP3 is formed in a direction vertical to an extending axis is, as illustrated in FIG. 4, configured such that the liquid junction part S31 is detachable from a fore end of the support tube S32, and adapted such that the liquid junction part S31 can be replaced in the case where a function as the liquid junction part S31 is reduced by contaminations due to continuous use or other cause.

The ammonium ion electrode S1 and the potassium ion electrode S2 that are respectively provided with the responsive membranes S11 and S21 and have the sensor planes SP1 and SP2 provided with being tilted with respect to extending axes of the sensors S1, S2 and S3 have substantially the same shapes.

The pressing mechanism 2 is one that collectively presses all of the sensors S1, S2, and S3 against the body 1. In the cross-sectional views, the pressing mechanism 2 is one that is illustrated as a substantially U-shaped member on the fore end surface of the ammonia meter 100, and substantially covers a fore end part of the body 1. Also, the pressing mechanism 2 is provided with four through-holes TH1, TH2, TH3, and TH4 for exposing the sensor planes SP1, SP2, and SP3 of the respective sensors S1, S2, and S3, and a fore end of the thermometer protecting tube P in a state of covering the fore end part of the body 1.

In the internal liquid S13 of the ammonium ion electrode S1 of the present embodiment, ammonium chloride is contained, and as the internal electrode S1E, an Ag/AgCl electrode is used. Also, the responsive membrane S11 is a membrane that selectively responds to an ammonium ion, and has properties as a semipermeable membrane. As such a membrane corresponding to each type of ions, specifically, a membrane made of, for example, an organic solvent, and polyvinyl chloride resin, silicone rubber, or the like supporting them is cited. On the other hand, as the internal liquid S33 of the reference electrode S3, a supersaturated potassium chloride solution is used, and as the internal electrode S3E, an Ag/AgCl electrode is used.

The membrane potential (mV) of the responsive membrane S11 of the ammonium ion electrode S1 can be represented by the following expression (1):

[Expression 2]

$$E = E°_{Ion} + \frac{RT}{F} \ln \overbrace{\left| \frac{a_{N,Sample}}{a_{N,Ion}} \times \frac{a_{Cl,Ref}}{a_{Cl,Ion}} \right|}^{B} \quad (1)$$

Here, respective parameters in the expression (1) are as follows:

E: the membrane potential (mV) of the responsive membrane S11 of the ammonium ion electrode S1, $E°_{Ion}$: the reference electrode potential (mV) for the ammonium ion electrode S1, R: the gas constant, F: the Faraday constant, T: absolute temperature (K), $a_{N,Sample}$: $NH_4^+$ ion activity (mol/L) in the analyzing target liquid L, $a_{N,Ion}$: $NH_4^+$ ion activity (mol/L) in the internal liquid S13 of the ammonium ion electrode S1, $a_{Cl,Ref}$: $Cl^-$ ion activity (mol/L) in the internal liquid S33 of the reference electrode S3, and $a_{Cl,Ion}$: $Cl^-$ ion activity (mol/L) in the internal liquid S13 of the ammonium ion electrode S1.

In the present embodiment, the ion activity (ion concentration) of each type of the ions is regulated such that a point at which the whole of a B term surrounded by a solid line in the expression (1) becomes equal to 1 falls within a measurable concentration range, and thereby within a concentration range of the ammonium ion in the analyzing target liquid L, i.e., within a measurement range, an isothermal point can be obtained. Further, in the present embodiment, the concentration of the ammonium ion and the concentration of the chloride ion in the internal liquid S13 are regulated such that an osmotic pressure of the internal liquid S13 reaches the same level as an osmotic pressure of the analyzing target liquid L. Note that simulation may be performed on the basis of the expression (1) to prepare the internal liquid such that the isothermal point falls within the measurement range.

According to the ammonium meter 100 of the present embodiment configured as described, by varying the concentration of the ammonium ion and the concentration of the chloride ion in the internal liquid S13 of the ammonium ion electrode S1, while the preparation is made such that the osmotic pressure of the internal liquid S13 reaches the same level as the osmotic pressure of the analyzing target liquid L, the isothermal point can be obtained within the concentration range of the ammonium ion in the analyzing target liquid L, so that even in the case where the responsive membrane S11 is a semipermeable membrane and the analyzing target liquid L having low ammonium ion concentration is set as a measuring target, water molecules do not permeate the internal liquid S13, and further, a measurement error associated with a temperature change can be reduced.

Note that the present invention is not limited to the above-described embodiment.

For example, the osmotic pressure of the internal liquid S13 depends not only on the concentration of the ammonium ion and the concentration of the chloride ion, but on total ion concentration of solutes, and therefore the osmotic pressure may be finely regulated by adding another electrolyte such as CaCl2 to the internal solution S13.

As the internal electrode used for the ion electrode according to the present invention, without limitation to the Ag/AgCl electrode, another electrode of which a potential is determined by specific ion concentration can also be used. Other electrodes as described above include electrodes such as various types of silver halide electrodes and mercury halide electrodes such as an Ag/AgBr electrode, Ag/AgI electrode, and Hg/HgBr electrode.

Also, as the internal liquid used for the ion electrode according to the present invention, without limitation to the $NH_4Cl$ solution, it is only necessary to appropriately select internal liquid depending on the type of an ion electrode, and for example, in the case of the potassium ion electrode, a KCl solution can be used; in the case of a calcium ion electrode, a CaCl2 solution can be used; and in the case of a sodium ion electrode, a solution such as an NaCl, NaBr, or NaI solution can be used.

Besides, it should be appreciated that parts or all of the above-described embodiment and variations may be appropriately combined, and various modifications can be made without departing from the scope of the present invention.

EXAMPLE

In order to confirm an effect of the present invention, a test as described below was done.

<Test Conditions>

As the reference electrode, an electrode of which an internal electrode was an Ag/AgCl electrode, and internal liquid was a 3.33 M potassium chloride solution was used. On the other hand, the internal liquid of the ammonium ion electrode was prepared such that the isothermal point was 0.0000714 M (1 ppm·N) and the osmotic pressure was the same as that of a solution having a salt concentration of 0.03 M.

The reference electrode and ammonium ion electrode respectively having the above configurations were used to, while changing temperature, confirm whether or not an electrode response followed a calculation expression. A result is illustrated in a graph of FIG. 6.

Figure 6:
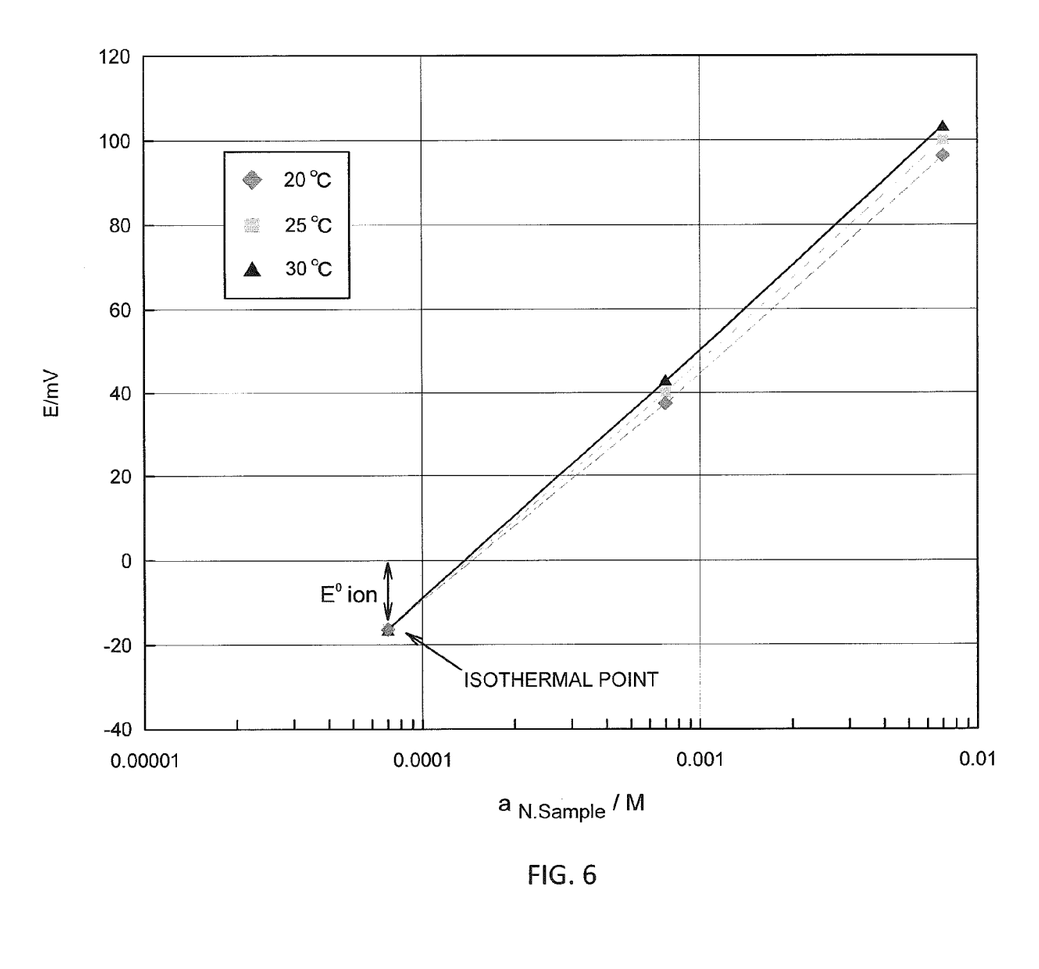
FIG. 6 is a graph illustrating a test result in an example.

As illustrated in the graph of FIG. 6, it was confirmed that the isothermal point was an ammonium ion concentration of 0.0000714 M (1 ppm·N). Note that in the case where the isothermal point shifts from the measurable concentration range and a measured value E within the measurable concentration range does not completely follow the expression (1), a gap is increased between E expected from the expression (1) and an actual measured value E, and therefore a measurement error increases.

EXPLANATIONS OF LETTERS OR NUMERALS

S1: Ammonium ion electrode
S11: Responsive membrane
S13: Internal liquid

The invention claimed is:

1. A liquid analyzer comprising:
a reference electrode that is provided with internal liquid containing a halide ion and an internal electrode in contact with the internal liquid in a space communicatively connected outside through a liquid junction part; and
an ion electrode that is provided with internal liquid and an internal electrode in contact with the internal liquid in a space separated from outside by a responsive membrane, and has a measurable concentration range for a measuring target ion, the measurable concentration range being lower than concentration of the halide ion in the internal liquid of the reference electrode, wherein:

the internal liquid of the ion electrode contains the measuring target ion and a halide ion;

the concentration of the halide ion in the internal liquid of the ion electrode is different from the concentration of the halide ion in the internal liquid of the reference electrode; and the concentration of the measuring target ion and the concentration of the halide ion in the internal liquid of the ion electrode are such that an osmotic pressure and an isothermal point of the internal liquid of the ion electrode respectively have desired values, and the isothermal point is included in the measurable concentration range.

2. The liquid analyzer according to claim 1, wherein the responsive membrane of the ion electrode has a property of a semipermeable membrane.

3. The liquid analyzer according to claim 1, wherein the internal electrode of the ion electrode is an Ag/AgCl electrode.

4. A method for preparing internal liquid of an ion electrode that is provided with the internal liquid and an internal electrode in contact with the internal liquid in a space separated from outside by a responsive membrane, and has a measurable concentration range for a measuring target ion, the measurable concentration range being lower than concentration of a halide ion in internal liquid of a reference electrode, wherein:

the internal liquid of the ion electrode contains the measuring target ion and a halide ion; and the internal liquid of the ion electrode is prepared on a basis of concentration of the measuring target ion and concentration of the halide ion in the internal liquid of the ion electrode, the internal liquid being prescribed such that the concentration of the halide ion in the internal liquid of the ion electrode is different from the concentration of the halide ion in the internal liquid of the reference electrode, such that an osmotic pressure and an isothermal point of the internal liquid of the ion electrode respectively have desired values, and the isothermal point is included in the measurable concentration range.

* * * * *